United States Patent [19]

Eppstein

[11] Patent Number: 4,606,917

[45] Date of Patent: Aug. 19, 1986

[54] SYNERGISTIC ANTIVIRAL COMPOSITION

[75] Inventor: Deborah A. Eppstein, Los Altos, Calif.

[73] Assignee: Syntex (U.S.A) Inc., Palo Alto, Calif.

[21] Appl. No.: 656,221

[22] Filed: Oct. 3, 1984

[51] Int. Cl.[4] .................. A61K 45/02; C12P 21/00
[52] U.S. Cl. ...................................... 424/85; 435/68; 435/804
[58] Field of Search .................. 424/85; 435/68; 260/112 R, 112.5 R; 422/61

[56] References Cited

U.S. PATENT DOCUMENTS 4,462,986  7/1984  Smith .................................. 424/85

FOREIGN PATENT DOCUMENTS 0109748  5/1984  European Pat. Off. .

OTHER PUBLICATIONS

Eppstein et al., Biochem. Biophys. Res. Comm., vol. 120, pp. 66–73, 1984.

Primary Examiner—Blondel Hazel
Attorney, Agent, or Firm—Grant D. Green; Tom M. Moran; Alan M. Krubiner

[57] ABSTRACT

Combinations of 9-(1,3-dihydroxy-2-propoxymethyl) guanine or a pharmaceutically acceptable salt thereof, with $\beta$-interferon show a surprisingly high degree of synergism in their activity against viral infections.

6 Claims, No Drawings

SYNERGISTIC ANTIVIRAL COMPOSITION

BACKGROUND OF THE INVENTION

1. Field of the Invention

This invention relates to an antiviral composition comprising 9-(1,3-dihydroxy-2-propoxymethyl)guanine (DHPG) and β-interferon (β-IFN). This invention also relates to a method of treating viral infections using the above composition or by co-administration of DHPG and β-interferon.

2. Related Disclosure

The compound 9-(1,3-dihydroxy-2-propoxymethyl)-guanine is known to be a potent antiviral agent. See, for example, U.S. Pat. No. 4,355,032. It is known to combine interferon with the antiviral compound acyclovir. See *Infect.Immun.* 32, 995–9 (1981), *Antimicrob. Agents Chemother.* 19, 672–4 (1981) and *Arch. Virol* 73, 135–143 (1982).

It is known that the combinaton of DHPG and α-interferon and/or γ-interferon produces a synergistic effect and is a more potent antiviral agent than DHPG or interferon alone. See, e.g., U.S. Pat. No. 4,462,986.

It has now feen found that the combination of DHPG with β-interferon is surprisingly more synergistic than the combination of DHPG with either or both α- or γ-interferon.

SUMMARY OF THE INVENTION

One aspect of the invention is an antiviral composition comprising 9-(1,3-dihydroxy-2-propoxymethyl)-guanine or a pharmaceutically acceptable salt thereof and β-interferon.

Another aspect of the invention is the method of treating viral infections in a mammal by administering an effective amount of β-interferon and an effective amount of 9-(1,3-dihydroxy-2-propoxymethyl)guanine or a pharmaceutically acceptable salt to a mammal having a viral infection.

Another aspect of the invention is an antiviral pharmaceutical composition comprising β-interferon and DHPG or a pharmaceutically acceptable salt in a topical formulation.

Another aspect of the invention is an article of manufacture for co-administration comprising two containers, one container containing 9-(1,3-dihydroxy-2-propoxymethyl)guanine or a pharmaceutically acceptable salt with a pharmaceutically acceptable excipient, and another container containing natural, recombinant, or modified β-interferon with a pharmaceutically acceptable excipient.

DETAILED DESCRIPTION AND PREFERRED EMBODIMENTS

β-interferon is derived from mammalian cells such as fibroblast cells. As used herein, "β-interferon" includes β-interferon derived both from natural sources, including human, bovine, and equine, and by recombinant DNA techniques. It also includes modified forms of β-interferon; e.g., by glycosylation, methylation, substitution and/or deletion of a limited number of amino acids. As used herein, HuIFN-β refers to human β-interferon, and rHuIFN-β refers to HuIFN-β produced using recombinant techniques. IFN-$β_{ser-17}$ refers to β-interferon in which the seventeenth amino acid has been replaced with serine.

Interferon concentrations are commonly expressed as standard "units" which are internationally accepted and documented, and relate to the potency of a given quantity of interferon to inhibit virus replication under standard conditions.

9-(1,3-Dihydroxy-2-propoxymethyl)guanine, sometimes referred to herein as DHPG, has the following structure:

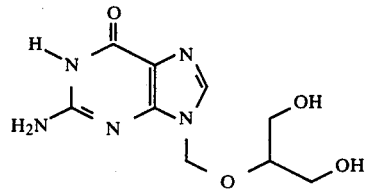

DHPG may be used as the free base, as a pharmaceutically acceptable salt, or as a mixture thereof.

The broadest statement of the invention is a composition comprising DHPG or a pharmaceutically acceptable salt thereof and β-interferon.

A preferred form of the invention is a composition comprising DHPG and a form of human β-interferon.

Another preferred embodiment of the invention is the composition comprising DHPG with bovine β-interferon.

Another preferred embodiment of the invention is the composition comprising DHPG with equine β-interferon.

A more preferred embodiment of the invention is a composition comprising DHPG and recombinant human β-interferon.

Another preferred embodiment is the composition comprising effective amounts of human β-interferon and DHPG in a form suitable for topical application, e.g., as a cream, ointment, or gel.

Another preferred embodiment is the article of manufacture comprising a vial containing DHPG or a pharmaceutically acceptable salt thereof with a pharmaceutically acceptable excipient and a vial containing β-interferon with a pharmaceutically acceptable excipient, in a form suitable for co-administration, either simultaneously or sequentially, including administration of DHPG and IFN-β at unequal time intervals.

The most preferred embodiment is an ointment for topical application comprising therapeutically effective amounts of recombinant human $β$-interferon$_{ser-17}$ and DHPG.

The process for making DHPG and its pharmaceutically acceptable salts is taught in U.S. Pat. No. 4,355,032, which is incorporated herein by reference. β-interferon may be collected from natural sources by methods well taught in the art (for example, as by the methods taught in U.S. Pat. No. 4,007,086, incorporated herein by reference), or may be obtained through recombinant DNA techniques. β-interferon may be purified, e.g., by the process taught by U.S. Pat. No. 4,450,103, which is incorporated herein by reference, and by other methods taught in the art [see e.g., Tan, Y. H. et al, *J. Biol. Chem.*, 254: 8067–73 (1979), Knight, Jr. E., et al, *Science,* 207: 525–26 (1979), Okamura H. et al, *Biochemistry,* 19, 3831–35 (1980)]. The rHuIFN-$β_{ser-17}$ used in the examples was obtained from Cetus Corp., but may be made by the following method.

IFN-$β_{ser-17}$ is best produced by modifying DNA sequences which code for IFN-β, the manipulating microorganisms to express the modified DNA as protein. When the first base of codon 17 (thymine) of the sense strand of the DNA sequence which codes for the mature IFN-β is replaced with adenine, the cysteine residue at position 17 in the amino acid sequence of IFN-β is replaced by serine. By changing T to other bases, and by changing other bases in codon 17, cysteine may be replaced with other amino acids. The site-specific mutagenesis is induced using a synthetic 17-nucleotide primer having the sequence GCAATTTTCAGAGTCAG which is identical to a seventeen nucleotide sequence on the sense strand of IFN-β in the region of codon 17 except for a single base mismatch at the first base of codon 17. (As used herein, C=deoxycytidine, T=deoxythymidine, A=deoxyadenosine, and G=deoxyguanosine.) The mismatch is at nucleotide 12 in the primer. The 17-mer is hydridized to single-stranded M13 phage DNA which carries the antisense strand of the IFN-β gene. The oligonucleotide primer is then extended on the DNA using DNA polymerase I Klenow fragment (a fragment of DNA polymerase I lacking the 5'-exonuclease subunit) and the resulting double-strand DNA (dsDNA) is converted to closed circular DNA with $T_4$ ligase. Replication of the resulting mutational heteroduplex yields clones from the DNA strand containing the mismatch. Mutant clones may be identified and screened by the appearance or disappearance of specific restriction sites, antibiotic resistance or sensitivity, or by other methods known in the art. When cysteine is substituted by serine, the substitution of T by A results in the creation of a new HinfI restriction site in the structural gene. (A restriction site is a point in a DNA sequence that is recognized and cleaved by a particular restriction enzyme. A HinfI restriction site is a restriction site recognized by HinfI endonuclease.) The mutant clone is identified by using the oligonucleotide primer as a probe in a hybridization screening of the mutated phage plaques. The primer will have a single mismatch when hybridized to the parent but will have a perfect match when hybridized to the mutated phage DNA. Hybridization conditions can then be devised where the oligonucleotide primer will preferentially hybridize to the mutated DNA but not to the parent DNA. The newly generated HinfI site also serves as a means of confirming the single base mutation in the IFN-β gene.

The M13 phage DNA carrying the mutated gene is isolated and spliced into an appropriate expression vector, such as plasmid pTrp3, and *E. coli* strain MM294 is transformed with the vector. Suitable growth media for culturing the transformants and their progeny are known to those skilled in the art. The expressed mutein (protein derived from a mutated gene) of IFN-β is isolated, purified and characterized.

UTILITY AND ADMINISTRATION

The subject composition exhibits potent antiviral activity when administered to mammals. For example, the composition of the present invention exhibits excellent activity against herpes simplex virus 1 and 2 and related viruses such as cytomegalovirus, Epstein-Barr virus and varicella zoster virus, as well as viral hepatitis such as hepatitis B.

Pharmaceutical compositions, both veterinary and human, containing the subject composition appropriate for antiviral use are prepared by methods and contain excipients which are well known in the art. A generally recognized compendium of such methods and ingredients is *Remington's Pharmaceutical Sciences* by E. W. Martin, (Mark Publ. Co., 15th Ed., 1975). Liposomes may also be employed in compositions of the invention, using methods known in the art [for example, as described in Szoka, F. Jr., et al, *Ann. Rev. Biophys. Bioeng.* 9:467–508 (1980): Schullery, S. E. et al, *Biochemistry* 19:3919–23 (1980); Gregoriadis, G., et al, "Liposomes in Biological Systems:", John Wiley and Sons (1980), and Gregoriadis, G. (Ed.) "Liposome Technology", CRC Press, Inc. (1984).].

When the composition of the invention is administered by methods other than topical application, it may be desirable to administer the DHPG component and the β-interferon component at different times, and/or at different frequencies. Also, the components need not be administered by the same method, e.g., DHPG may be administered orally twice daily while β-interferon is administered intramuscularly or topically.

The composition of the invention is effective in mammals, including e.g., humans, cattle, and horses, and may be administered parenterally (for example, by intravenous, subcutaneous, intraperitoneal, intralesional or intramuscular injection), orally, (DHPG component only), topically, rectally or intranasally.

DHPG is administered orally or parenterally at dose levels, calculated as the free base of DHPG, of about 0.01 to 300 mg/kg, preferably 0.1 to 10 mg/kg of mammal body weight, and is used in humans in a unit dosage form, administered one to five times daily in the amount of 1 to 500 mg per unit dose. For oral administration, fine powders or granules may contain diluting, dispersing and surface active agents, and may be presented in a draught, in water or in a syrup; in capsules or sachets in the dry state or in a non-aqueous solution or suspension, wherein suspending agents may be included; in tablets, wherein binders and lubricants may be included; in a suspension in water or a syrup; or in an aerosol. Where desirable or necessary, flavoring, preserving, suspending, thickening or emulsifying agents may be included. Tablets and granules are preferred, and these may be coated. The amount of DHPG in the formulation may vary from 0.1 percent weight (%w/w) to 99%w/w or more of the compound based on the total formulation and about 1%w/w to 99.9%w/w excipient. Preferably DHPG is present at a level of 10%–95%w/w.

For parenteral administration of the DHPG component or for administration as drops, as for eye infections, DHPG may be presented in aqueous solution in a concentration of from about 0.1 to 10% by weight for DHPG component, more preferably about 0.1 to 0.4%. The solution may contain pharmaceutically acceptable antioxidants, buffers, and other suitable additives.

The β-interferon component is administered parenterally in aqueous solution at dose levels of 10 to $10^7$ U/kg, preferablly $10^3$ to $10^5$ U/kg of body weight in man, administered once or twice a day for 1 to 7 days per week. For eye drops, the interferon is present at $10^3$–$10^9$ U/ml, preferably about $10^5$–$10^8$ U/ml.

Alternatively, for infections of the eye or other external tissues, e.g. mouth, skin, and genitalia, the compositions are preferably applied to the infected part of the patient's body topically as an ointment, cream, gel, aerosol or powder, preferably in an ointment or cream. The compounds may be presented in an ointment, for instance with a water-soluble ointment base, or in a cream, for instance with an oil-in-water cream base, in a concentration of from about 0.01 to 10% for the DHPG component; preferably 0.1 to 7%, most preferably about 3%w/v and in a concentration of $10^3$–$10^9$ U/g, preferably $10^5$–$10^8$ U/g for the interferon component. Additionally, viral infections may be treated by use of a sustained release drug delivery system such as is described in U.S. Pat. No. 4,217,898.

For aerosol administration, the active ingredient is preferably supplied in finely divided form or in a solution along with a surfactant and a propellant. Typical percentages of active ingredients are 0.001 to 20% by weight, preferably 0.004 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

PREPARATION 1

Cloning of the IFN-$\beta$ gene into M13 Vector

The use of M13 phage vector as a source of single-stranded DNA template has been demonstrated by G. F. Temple et al *Nature* (1982) 296:537–540. Plasmid p$\beta$ trp containing the IFN-$\beta$ gene, under control of *E. coli* trp promoter, is digested with the restriction enzymes HindIII and XhoII. The M13mp8 (J. Messing, "Third Cleveland Symposium on Macromolecules: Recombinant DNA," Ed. A. Walton, Elsevier Press, 143–153 (1981) replicative form (RF) DNA is digested with restriction enzymes HindIII and BamHI and mixed with the p$\beta$1 trp DNA which have previously been digested with HinDIII and XhoII. The mixture is then ligated with $T_4$ DNA ligase and the ligated DNA transformed into competent cells of *E. coli* strain JM 103 and plated on Xgal indicator plates (J. Messing et al, *Nucleic Acids Res* (1981) 9:309–321). Plaques containing recombinant phage (white plaques) are picked, inoculated into a fresh culture of JM 103 and minipreps of RF molecules prepared from the infected cells (H. D. Birnboim and J. Doly, *Nucleic Acid Res.* (1979) 7:1513–1523). The RF molecules are digested with various restriction enzymes to identify the clones containing the IFN-$\beta$ insert. Single-stranded (ss) phage DNA is prepared from clone M13-$\beta$1 to serve as a template for site-specific mutagenesis using a synthetic oligonucleotide.

PREPARATION 2

Site specific mutagenesis

Forty picomoles of the synthetic oligonucleotide GCAATTTTCAGAGTCAG (primer) is treated with $T_4$ kinase in the presence of 0.1 mM adenosine triphosphate (ATP). 50 mM hydroxymethylaminomethane hydrochloride (Tris-HCl) pH 8.0, 10 mM $MgCl_2$, 5 mM dithiothreitol (DTT) and 9 units of $T_4$ kinase, in 50 $\mu$l at 37° C. for 1 hr. The kinased primer (12 pmole) is hybridized to 5 $\mu$g of ss M13-$\beta$1 DNA in 50 $\mu$l of a mixture containing 50 mM NaCl, 10 mM tris-HCl, pH 8.0, 10 mM $MgCl_2$ and 10 mM $\beta$-mercaptoethanol by heating at 67° C. for 5 min and at 42° C. for 25 min. The annealed mixture is then chilled on ice and then added to 50 $\mu$l of a reaction mixture containing 0.5 mM each of deoxynucleotide triphosphate (DNTP), 80 mM Tris-HCl, pH 7.4, 8 mM $MgCl_2$, 100 mM NaCl, 9 units of DNA polymerase I Klenow fragment, 0.5 mM ATP and 2 units of $T_4$ DNA ligase, incubated at 37° C. for 3 hr and at 25° C. for 2 hr. The reaction is then terminated by phenol extraction and ethanol precipitation. The DNA is dissolved in 10 mM Tris-HCl pH 8.0, 10 mM ethylenediaminetetraacetic acid (EDTA), 50% sucrose and 0.05% bromophenylblue and electrophoresed on 0.8% agarose gel in the presence of 2 $\mu$g/ml of ethidium bromide. The DNA bands corresponding to the RF forms of M13-$\beta$1 are eluted from gel slices by the perchlorate method (R. W. Davis, et al, "Advanced Bacterial Genetics," Cold Spring Harbor Laboratory, N.Y., p. 178–179 (1980)). The eluted DNA is used to transform competent JM 103 cells, grown overnight and single strand (ss) DNA isolated from the culture supernatant. This ssDNA is used as a template in a second cycle of primer extension, the gel purified RF forms of the DNA are transformed into competent JM 103 cells, plated onto agar plates and incubated overnight to obtain phage plaques.

PREPARATION 3

Screening and identification of mutagenized plaques

Plates containing mutated M13-$\beta$1 plaques as well as two plates containing unmutated M13-$\beta$1 phage plaques are chilled to 4° C., and plaques from each plate transferred onto two nitrocellulose filter circles by layering a dry filter on the agar plate for 5 min for the first filter and 15 min for the second filter. The filters are then placed on thick filter papers soaked in 0.2N NaOh, 1.5M NaCl and 0.2% Triton X-100 for 5 min. and neutralized by layering onto filter papers soaked with 0.5M Tris-HCl, pH 7.5 and 1.5M NaCl for another 5 min. The filters are washed in a similar fashion twice on filters soaked in 2xSSC (standard saline citrate), dried and then baked in a vacuum oven at 80° C. for 2 hr. The duplicate filters are prehybridized at 55° C. for 4 hr. with 10 ml per filter of DNA hybridization buffer (5xSSC) pH 7.0 4xDenhardt's solution (polyvinyl-pyrrolidine, ficoll and bovine serum albumin, 1x=0.02% of each), 0.1% sodium dodecyl sulfate (SDS), 50 mM sodium phosphate buffer pH 7.0 and 100 $\mu$g/ml of denatured salmon sperm DNA. A $^{32}$P-labeled probe is prepared by kinasing the oligonucleotide primer with $^{32}$P-labeled ATP. The filters are hybridized to 3.5×$10^5$ cpm/ml of $^{32}$P-labeled primer in 5 ml per filter of DNA hybridization buffer at 55° C. for 24 hr. The filters are washed at 55° C. for 30 min. each in washing buffers containing 0.1% SDS and decreasing amounts of SSC. The filters are washed initially with buffer containing 2xSSC and the control filters containing unmutated M13-$\beta$1 plaques are checked for the presence of any radioactivity. The concentration of SSC is lowered stepwise and the filters washed until no detectable radioactivity remains on the control filters with the unmutated M13-$\beta$1 plaques. The filters are air dried and autoradiographed at $-70°$ C. for 2-3 days.

PREPARATION 4

Expression of mutated IFN-$\beta$ in E. coli

RF DNA from M13-SY2501 is digested with restriction enzymes HindIII and XhoII and the 520 bp insert fragment purified on a 1% agarose gel. The plasmid pTrp3 containing the E. coli trp promoter is digested with the enzymes HindIII and BamHI, mixed with the purified M13-SY2501 DNA fragment and ligated in the presence of T$_4$DNA ligase. The ligated DNA is transformed into E. coli strain MM294. Ampicillin resistant transformants are screened for sensitivity to the drug tetracycline. Plasmid DNA from five ampicillin resistant, tetracycline-sensitive clones are digested with HinfI to screen for the presence of the M13-SY2501 insert.

The plasmid designated as clone pSY2501 is available from the Agricultural Research Culture Collection (NRRL), Fermentation Laboratory, Northern Regional Research Center, Science and Education Administration, U.S. Department of Agriculture, 1815 North University Street, Peoria, Ill. 60604 and is assigned accession numbers CMCC No. 1533 and NRRL No. B-15356.

Cultures of pSY2501 and p$\beta$1trp are grown up to an optical density (DD$_{600}$) of 1.0. Cell free extracts are prepared and the amount of IFN-$\beta$ antiviral activity assayed on GM2767 cells in a microtiter assay.

PREPARATION 5

Purification of IFN-$\beta_{ser17}$

IFN-$\beta_{ser17}$ is recovered from E. coli which have been transformed to produce IFN-$\beta_{ser17}$. The E. coli are grown in the following growth medium to an OD of 10-11 at 680 nm (dry wt 8.4 g/l).

| Ingredient | Concentration |
|---|---|
| NH$_4$Cl | 20 mM |
| K$_2$SO$_4$ | 16.1 mM |
| KH$_2$PO$_4$ | 7.8 mM |
| Na$_2$HPO$_4$ | 12.2 mM |
| MgSO$_4$.7H$_2$O | 3mM |
| Na$_2$citrate.2H$_2$O | 1.5 mM |
| MnSO$_4$.4H$_2$O | 30 $\mu$M |
| ZnSO$_4$.7H$_2$O | 30 $\mu$M |
| CuSO$_4$.5H$_2$O | 3 $\mu$M |
| L-tryptophan | 70 mg/l |
| FeSO$_4$.7H$_2$O | 72 $\mu$M |
| thiamine HCl | 20 mg/l |
| glucose | 40 G/L |
| pH controlled with NH$_4$OH | |

A 9.9 l (9.9 kg) harvest of the transformed E. coli is cooled to 20° C. and concentrated by passing the harvest through a cross-flow filter at an average pressure drop of 110 kPa and steadystate filtrate flow rate of 260 ml/min until the filtrate weight is 8.8 kg. The concentrate (approximately one liter) is drained into a vessel and cooled to 15° C. The cells in the concentrate are then disrupted by passing the concentrate through a Mason-Gaulin homogenizer at 5° C. 69,000 kPa. The homogenizer is washed with one liter phosphate buffered saline, pH 7.4 (PBS), and the wash is added to the disruptate to give a final volume of two liters. This volume is continuously centrifuged at 12000xg at a 50 ml/min flow rate. The solid is separated from the supernatant and resuspended in four liters of PBS containing 2% by wt. SDS. This suspension is stirred at room temperature for 15 min after which there should be no visible suspended material. The solution is then extracted with a 2-butanol at a 1:1 2-butanol:solution volume ratio. The extraction is carried out in a liquid-liquid phase separator using a flow rate of 200 ml/min. The organic phase is then separated and evaporated to dryness to yield 21.3 g of protein. This may then be resuspended in distilled water at a 1:10 volume ratio.

EXAMPLE 1

Human embryonic tonsil (HET) cells were plated in 24 well dishes at 10$^5$ cells/well and incubated 24 hr until confluent monolayers were obtained. Cells were then treated for 24 hr with interferon $\alpha$, $\beta$, or $\gamma$ as indicated, or with media without interferon. The cells were subsequently washed and infected with herpes simplex virus type 2 (HSV-2) at a multiplicity of infection (MOI) of 5 plaque forming units (PFU) per cell. Virus was absorbed for 1 hr at 37° C., and the cells were then washed and the interferons and/or DHPG were added as indicated to triplicate wells. Cell-virus cultures were then incubated for 1 day, and the virus yield was subsequently determined by plaque assay in Vero cells.

As shown in Table 1, 0.03 $\mu$M DHPG alone reduced the yield of infectious HSV-2 by 1.9 fold. Treatment with interferons $\alpha_2$ or $\gamma$ alone at 200 U/ml did not significantly affect virus yield, while treatment with interferon $\alpha_1$ or $\beta$ reduced virus yield by 1.4 and 2.7 fold respectively. However, the most striking reduction in virus yield was obtained by the combination of DHPG and $\beta$-interferon, resulting in a 1750-fold reduction in virus yield.

TABLE 1

Inhibition of Growth of HSV-2 by Interferons Alone or in Combination with DHPG

| DHPG | Interferon type: (IU/ml) | Ratio of Virus Yield (Untreated/Treated) | | | | |
|---|---|---|---|---|---|---|
| | | none | $\alpha_1$ | $\alpha_2$ | $\beta$-ser$_{17}$ | $\gamma$ |
| 0 | 0 | ≡ 1 | — | — | — | — |
| 0.03 | 0 | 1.9 | — | — | — | — |
| 0 | 200 | — | 1.4 | 0.9 | 2.7 | 1.0 |
| 0.03 | 200 | — | 250. | 100 | 1750 | 10 |

This unexpected and surprising synergistic reduction of virus yield by DHPG/$\beta$-interferon combination was significantly greater than the reduction obtained by combination of DHPG with either $\alpha$ or $\gamma$ interferons. As shown in Table 2, the relative increase in fold reduction of virus by $\beta$-interferon/DHPG combination vs $\alpha_1$, $\alpha_2$, or $\gamma$-interferon/DHPG combination ranged from 7 to 175 fold. Thus the $\beta$-interferon/DHPG combination was significantly more potent in inhibiting viral growth than were the $\alpha$ or $\gamma$-interferon/DHPG combinations.

TABLE 2

Increase in Synergy of $\beta$-interferon/DHPG Combination vs. $\alpha_1$, $\alpha_2$, or $\gamma$-interferon/DHPG Combinations Increase in Fold Reduction of Virus Yield by $\beta$-IFN

TABLE 2-continued
Increase in Synergy of β-interferon/DHPG Combination vs.
$\alpha_1$, $\alpha_2$, or γ-interferon/DHPG Combinations

| $\dfrac{(\beta\text{-IFN}+\text{DHPG})}{(\alpha_1\text{-IFN}+\text{DHPG})}$ | $\dfrac{(\beta\text{-IFN}+\text{DHPG})}{(\alpha_2\text{-IFN}+\text{DHPG})}$ | $\dfrac{(\beta\text{-IFN}+\text{DHPG})}{(\gamma\text{-IFN}+\text{DHPG})}$ |
|---|---|---|
| 7 | 18 | 175 |

EXAMPLE 2

HET cells were treated with interferons and/or DHPG as described in Example 1, except that additional cultures were treated similarly with 9-(2-hydroxy-1-ethoxymethyl)guanine (ACV, acyclovir) with or without the various interferons. The results show that the antiherpetic synergy between DHPG and β-interferon was significantly greater (50–120 fold) than the combination of ACV and β-interferon. Also, the increased antiherpetic activity of the DHPG/β-interferon combination vs the ACV/β-interferon combination was additionally much greater than the increased antiherpetic activity of DHPG/α-interferon over that of ACV/α-interferon, as well as that of DHPG/γ-interferon over that of ACV/γ-interferon (Table 3).

TABLE 3
Increased Inhibition of HSV-2 Growth by DHPG-Interferon Treatment as Compared to ACV-Interferon Treatment

| rHuIFN Type | IU/ml | DHPG or ACV (μM) | Ratio of HSV-2 Yield (ACV + IFN/DHPG + IFN) |
|---|---|---|---|
| none | — | 0.03 | 1.0 |
|  | — | 0.1 | 2.0 |
| $\alpha_1$ | 200 | 0.03 | 50 |
|  | 100 | 0.07 | 20 |
| $\alpha_2$ | 200 | 0.03 | 20 |
|  | 100 | 0.07 | 10 |
| $\beta\text{-ser}_{17}$ | 200 | 0.03 | 120 |
|  | 100 | 0.07 | 50 |
| γ | 200 | 0.03 | 3 |

Thus the above results show that DHPG is strikingly synergistic with β-interferon in inhibiting growth of herpes simplex virus (1750 fold reduction in virus yield vs 2–3 fold reduction by either DHPG or β-interferon alone), and that the combination of DHPG with β-interferon is surprisingly more effective (7–175 fold more effective) than is the comparable combination of DHPG with either α or γ interferons (Example 1). Furthermore, our results show that the antiherpetic synergism obtained by DHPG in combination with β-interferon is substantially more effective (up to 120 times) than is a comparable combination of ACV with β-interferon (Example 2).

EXAMPLE 3

The following example illustrates the preparation of representative pharmaceutical formulations containing DHPG and human β-interferon.

| A. Topical Formulation | |
|---|---|
| DHPG | 5.0 |
| β-Interferon | $10.^8$ U |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water qs | 100 ml |

All of the above ingredients, except water and interferon, are combined and heated at 60° C. with stirring. A sufficient quantity of water at 60° C. is then added with vigorous stirring to provide 90–99 g of the cream which is then cooled. The interferon which may be mixed with stabilizers such as albumin, dextrose, and pH buffering agents, is dissolved in 1–10 ml water to bring the total cream formulation to 100 g, and is then added with sufficient stirring, and the cream formulation is then cooled to room temperature or lower.

The following formulation is useful for intraperitoneal, subcutaneous, intralesional and intramuscular injection.

| B. IP, SC, IL and IM Formulation | |
|---|---|
| DHPG | 300.0 mg |
| β-Interferon | $2 \times 10.0^7$ U |
| Propylene glycol | 20 g |
| Polyethylene glycol | 20 g |
| Tween 80 | 1 g |
| 0.9% Saline solution qs | 100 ml |

The DHPG and β-interferon are dissolved in propylene glycol, polyethylene glycol 400 and Tween 80. A sufficient quantity of 0.9% saline solution is then added with stirring to provide 100 ml of the IP, SC, IL or IM solution which is filtered through a 0.2 micron membrane filter and packaged under sterile conditions.

The following formulation is useful for intravenous injection.

| C. I.V. Formulation | |
|---|---|
| DHPG | 300 mg |
| β-Interferon | $10^6$ U |
| Polysorbate 80 | 0.1 g |
| Propylene glycol or polyethylene glycol 400 | 3.0 g |
| Water qs | 100 ml |

The active compounds are added to a solution of polysorbate 80 and propylene glycol or polyethylene glycol 400 in 20 ml of water and mixed. The resulting solution is diluted with water to 100 ml and filtered through the appropriate 0.2 micron membrane filter.

| D. Tablet Formulation | |
|---|---|
|  | Parts by weight |
| DHPG | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg of active DHPG compound) with an appropriate tableting machine. (β-interferon is co-administered non-orally, e.g., topically, intramuscularly, intravenously, subcutaneously, intralesionally).

What is claimed is:

1. A composition comprising an effective amount of human β-interferon(ser 17) and 9-(1,3-dihydroxy-2-propoxymethyl)guanine or a pharmaceutically acceptable salt thereof.

2. An antiviral pharmaceutical composition which comprises an effective amount of the composition of claim 1 and a pharmaceutically acceptable carrier.

3. The antiviral pharmaceutical composition of claim 2, which is suitable for topical application.

4. A method of treating viral infections in a mammal having a viral infection which comprises administering an effective amount of the composition of claim 1.

5. An article of manufacture for treating a viral infection with an effective amount of human β-interferon(ser 17) and 9-(1,3-dihydroxy-2-propoxymethyl)guanine in a synergistic ratio, which article of manufacture comprises:
- a first container containing human β-interferon(ser 17) and a first pharmaceutically acceptable excipient suitable for parenteral administration; and
- a second container containing 9-(1,3-dihydroxy-2-propoxymethyl)guanine or a pharmaceutically acceptable salt thereof and a second pharmaceutically acceptable excipient.

6. The article of manufacture of claim 5 wherein said second pharmaceutically acceptable excipient is suitable for oral administration.

* * * * *